(12) United States Patent
Hirose

(10) Patent No.: US 9,339,185 B2
(45) Date of Patent: May 17, 2016

(54) IMAGING APPARATUS THAT ACQUIRES A FIRST IMAGE AND, VIA AN ABERRATION CORRECTION UNIT, A SECOND IMAGE OF AN AREA CORRESPONDING TO A PART OF THE FIRST IMAGE

(71) Applicant: CANON KABUSHIKI KAISHA, Tokyo (JP)

(72) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 134 days.

(21) Appl. No.: 13/760,359

(22) Filed: Feb. 6, 2013

(65) Prior Publication Data

US 2013/0215385 A1 Aug. 22, 2013

(30) Foreign Application Priority Data

Feb. 21, 2012 (JP) ................................. 2012-035088
Dec. 14, 2012 (JP) ................................. 2012-273761

(51) Int. Cl.
*A61B 3/14* (2006.01)
*A61B 3/00* (2006.01)
*A61B 3/10* (2006.01)
*A61B 3/15* (2006.01)

(52) U.S. Cl.
CPC ................. *A61B 3/14* (2013.01); *A61B 3/0091* (2013.01); *A61B 3/1025* (2013.01); *A61B 3/152* (2013.01)

(58) Field of Classification Search
CPC .......... A61B 3/1025; A61B 3/14; A61B 3/15; A61B 3/152; A61B 3/0091
USPC .......................................... 351/206; 600/425
See application file for complete search history.

(56) References Cited

U.S. PATENT DOCUMENTS

| 7,540,614 | B2 | 6/2009 | Kawashima et al. | |
|---|---|---|---|---|
| 7,758,189 | B2 * | 7/2010 | Hammer et al. | 351/206 |
| 7,824,035 | B2 * | 11/2010 | Yamada et al. | 351/206 |
| 8,002,411 | B2 * | 8/2011 | Kishida | A61B 3/14 351/205 |
| 8,235,528 | B2 | 8/2012 | Mukai et al. | |
| 8,308,297 | B2 | 11/2012 | Hirose et al. | |
| 8,390,818 | B2 | 3/2013 | Hirose et al. | |
| 2008/0158508 | A1 | 7/2008 | Kawashima et al. | |
| 2009/0091766 | A1 | 4/2009 | Hirose | |
| 2009/0285354 | A1 | 11/2009 | Hirose et al. | |
| 2010/0277692 | A1 | 11/2010 | Mukai et al. | |
| 2011/0102740 | A1 * | 5/2011 | Hirose | 351/206 |
| 2011/0234975 | A1 | 9/2011 | Hirose | |
| 2011/0273668 | A1 | 11/2011 | Hirose | |
| 2011/0301455 | A1 | 12/2011 | Numajiri et al. | |
| 2012/0044455 | A1 | 2/2012 | Hirose | |
| 2012/0293770 | A1 | 11/2012 | Hirose | |
| 2012/0320338 | A1 | 12/2012 | Hirose et al. | |

FOREIGN PATENT DOCUMENTS

JP 2008-161406 A 7/2008
JP 2010-259543 A 11/2010

*Primary Examiner* — Zachary Wilkes
(74) *Attorney, Agent, or Firm* — Fitzpatrick, Cella, Harper & Scinto

(57) ABSTRACT

In order to reduce a measurement range of an aberration of an eye to be inspected, provided is an imaging apparatus, including: a first image acquiring unit for acquiring a first image of the eye based on first return light from the eye irradiated with first measuring light via a first focus unit for focusing the first measuring light on the eye; a second image acquiring, by using an aberration correction unit, unit for acquiring a second image of an area corresponding to a part of the first image of the eye based on second return light from the object to be inspected irradiated with second measuring light via a second focus unit for focusing the second measuring light on the eye; and a focus adjustment unit for adjusting a focus condition of the second focus unit based on a focus condition of the first focus unit.

27 Claims, 4 Drawing Sheets

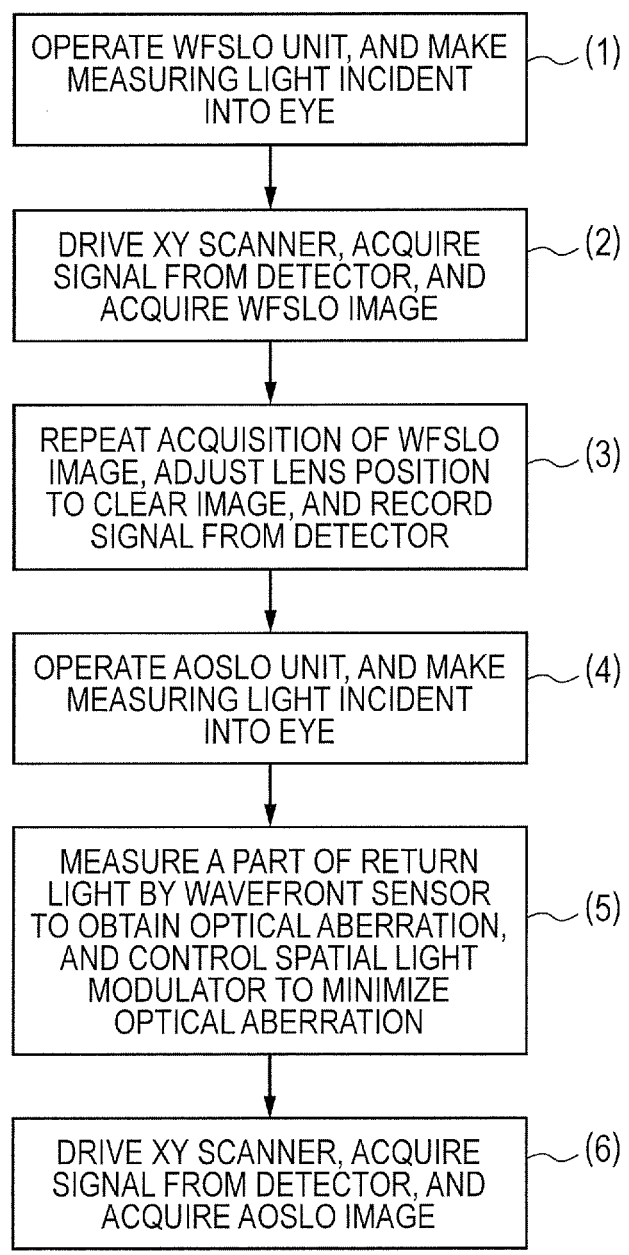

IMAGING APPARATUS THAT ACQUIRES A FIRST IMAGE AND, VIA AN ABERRATION CORRECTION UNIT, A SECOND IMAGE OF AN AREA CORRESPONDING TO A PART OF THE FIRST IMAGE

BACKGROUND OF THE INVENTION

1. Field of the Invention

The present invention relates to an imaging apparatus, and more particularly, to an optical image imaging apparatus or imaging apparatus that is used for ophthalmological diagnosis and treatment or the like.

2. Description of the Related Art

A scanning laser ophthalmoscope (SLO) which uses a principle of a confocal laser microscope is an ophthalmological apparatus that performs a raster scanning on a fundus of the eye with laser light which is measuring light and obtains a planar image of the fundus of the eye based on the intensity of return light with high resolution at high speed.

Such an apparatus for photographing or imaging a planar image is hereinafter referred to as SLO apparatus.

In recent years, it has become possible to acquire a planar image of a retina with improved lateral resolution by increasing a beam diameter of measuring light in the SLO apparatus. However, along with the increase in the beam diameter of measuring light, there occurs a problem of decreases in an SN ratio and the resolution of a planar image of a retina due to an aberration of an eye to be inspected when the planar image is acquired.

In order to solve the problem, there is developed an adaptive optics SLO apparatus including an adaptive optics system, in which an aberration of an eye to be inspected is measured by a wavefront sensor in real time, and aberrations of measuring light and return light thereof generated in the eye to be inspected are corrected by a wavefront correction device. Thus, it is possible to acquire a planar image with high lateral resolution.

When a planar image with high lateral resolution is acquired, because of problems of optical aberrations of the apparatus itself and a longer imaging time, an imaging range of a single image becomes smaller. As a result, there is a tendency that it becomes difficult to distinguish which part of the fundus the planar image corresponds to. In Japanese Patent Application Laid-Open No. 2010-259543, there is proposed a complex apparatus in which an SLO apparatus having a large field angle and an SLO apparatus having a small field angle with high resolution are combined so as to solve the problem.

When the aberration of the eye to be inspected is corrected by the wavefront correction device, the aberration of the device itself or its optical system may become a problem. In Japanese Patent Application Laid-Open No. 2008-161406, a mechanism for correcting a very small spherical aberration generated by an adaptive optics system is disposed so that a clear fundus image can be acquired.

As the fundus imaging apparatus described in Japanese Patent Application Laid-Open No. 2010-259543, as described above, the complex apparatus is proposed, in which the SLO apparatus having a large field angle and the SLO apparatus having a small field angle with high resolution are combined. Thus, a high resolution fundus image can be acquired efficiently.

In addition, in the ophthalmological apparatus described in Japanese Patent Application Laid-Open No. 2008-161406, the mechanism for correcting a very small spherical aberration generated by the adaptive optics system is disposed as described above, and hence a clear fundus image can be acquired.

Here, a measurement range of the wavefront sensor is determined in assumption of high ametropia (for example, −10 D to +5 D). In the case of Shack-Hartmann sensor that is a typical wavefront sensor, the measurement range and measurement accuracy have a trade-off relationship in principle. Therefore, the measurement accuracy is low in the case of low ametropia. In the conventional technologies described in Japanese Patent Application Laid-Open No. 2010-259543 and Japanese Patent Application Laid-Open No. 2008-161406, the aberration of the eye to be inspected, and the measurement range and measurement accuracy of the wavefront sensor are not taken into account, and hence there is a room for improvement.

SUMMARY OF THE INVENTION

In view of the problem described above, the present invention is to provide an imaging apparatus having higher resolution, which can perform aberration correction with high accuracy by minimizing a measurement range of a wavefront sensor for measuring an aberration of an eye to be inspected as an object to be inspected so as to enhance measurement accuracy of the aberration.

In order to achieve the above-mentioned object, according to an exemplary embodiment of the present invention, there is provided an imaging apparatus, including: a first image acquiring unit for acquiring a first image of an object to be inspected based on first return light from the object to be inspected irradiated with first measuring light via a first focus unit for focusing the first measuring light on the object to be inspected, a second image acquiring unit for acquiring, by using an aberration correction unit, a second image of an area corresponding to a part of the first image of the object to be inspected based on second return light from the object to be inspected irradiated with second measuring light via a second focus unit for focusing the second measuring light on the object to be inspected; and a focus adjustment unit for adjusting a focus condition of the second focus unit based on a focus condition of the first focus unit.

In view of the problem described above, according to the present invention, it is possible to realize the imaging apparatus having higher resolution, which can perform aberration correction with high accuracy with respect to an eye to be inspected as the object to be inspected.

Further features of the present invention will become apparent from the following description of exemplary embodiments with reference to the attached drawings.

BRIEF DESCRIPTION OF THE DRAWINGS

FIG. 3 is a diagram illustrating a procedure of acquiring an image by the SLO apparatus according to the first embodiment of the present invention.

DESCRIPTION OF THE EMBODIMENTS

A mode for carrying out the present invention is described by way of the following embodiments.

Embodiments

Next, embodiments of the present invention are described.

First Embodiment

In the first embodiment, an adaptive optics scanning laser ophthalmoscope (AOSLO) apparatus to which the present invention is applied is described as an optical imaging apparatus. The AOSLO apparatus includes an adaptive optics system, and is an apparatus for photographing or imaging a planar image (AOSLO image) of a retina having high lateral resolution. In addition, for the purpose of aiding acquisition of the AOSLO image, a wide field scanning laser ophthalmoscope (WFSLO) apparatus is associated, which performs imaging of a planar image having a wide field angle (WFSLO image).

In this embodiment, the AOSLO apparatus is configured to acquire a planar image by correcting an optical aberration of an eye to be inspected by using a spatial light modulator, and hence a good planar image can be acquired regardless of a diopter scale and the optical aberration of the eye to be inspected.

Here, in order to photograph or image a planar image having high lateral resolution, the apparatus includes the adaptive optics system. However, the adaptive optics system may not be included as long as the configuration of the optical system can realize high resolution.

(Entire Apparatus)

Figure 1A:
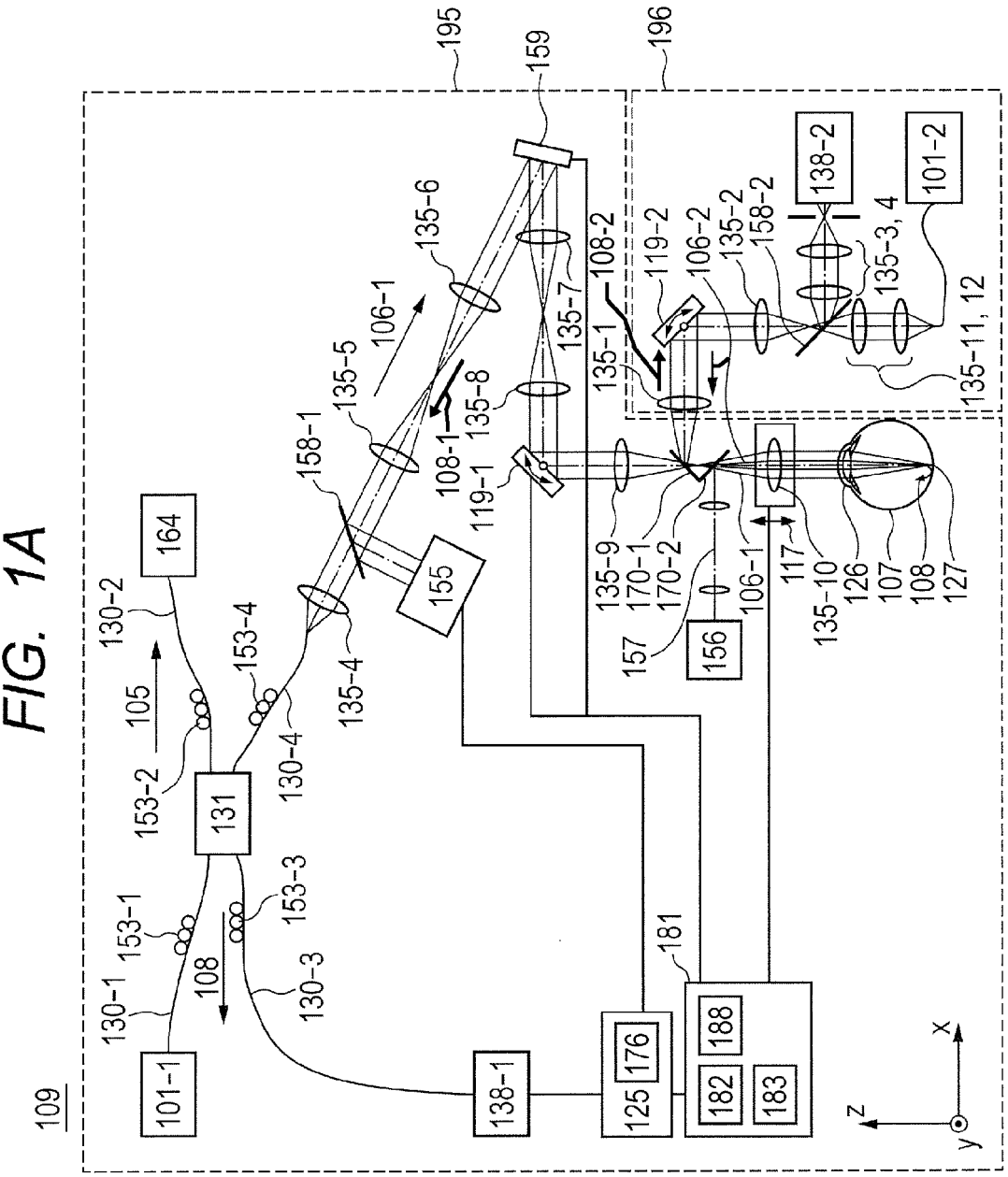
FIG. 1A is a diagram illustrating an entire structure of an SLO apparatus according to a first embodiment of the present invention.

First, a schematic configuration of an AOSLO apparatus 109 according to this embodiment is described specifically with reference to FIG. 1A.

The AOSLO apparatus 109 roughly includes an AOSLO unit 195 for acquiring the AOSLO image and a WFSLO unit 196 for acquiring a wide field SLO image (WFSLO image).

(Entire AOSLO Unit)

First, the entire AOSLO unit is described.

Light emitted from a light source 101-1 is split by an optical coupler 131 into reference light 105 and measuring light 106-1. The measuring light 106-1 is guided to an eye to be inspected 107 as an observation target through a single mode fiber 130-4, a spatial light modulator 159, an XY scanner 119-1, a dichroic mirror 170-2, and the like.

The AOSLO unit also includes a fixation lamp 156, and a light flux 157 from the fixation lamp 156 has a role of prompting the eye to be inspected 107 to fixate or rotate.

The measuring light 106-1 becomes return light 108 after being reflected or scattered by the eye to be inspected 107, and the return light 108 propagates in the opposite direction in the optical path and enters a detector 138-1 through the optical coupler 131. The detector 138-1 converts an optical intensity of the return light 108 into a voltage signal, which is used for forming a planar image of the eye to be inspected 107. In this embodiment, the entire optical system is mainly constituted of a refracting optical system using lenses. However, it is possible to constitute the optical system by using a reflecting optical system using spherical mirrors instead of the lenses.

In addition, a reflective spatial light modulator is used as an aberration correction device in this embodiment, but it is possible to use a transmissive spatial light modulator or a variable shape mirror.

(Light Source of AOSLO)

Next, details of the light source 101-1 are described. The light source 101-1 is a super luminescent diode (SLD) serving as a typical low-coherent light source. A wavelength of the light source 101-1 is 830 nm and a bandwidth thereof is 50 nm. Here, in order to acquire a planar image having little speckle noise, a low-coherent light source is selected. Further, although the SLD is selected as the light source in this embodiment, any type of light source may be used as long as the light source can emit low-coherent light. For example, an amplified spontaneous emission (ASE) light source may be used.

In view of the measurement of the eye, a suitable wavelength is a near infrared light wavelength. The wavelength affects the lateral resolution of the acquired planar image, and hence the wavelength is desired to be as short as possible. Therefore, in this embodiment, the wavelength is set to 830 nm. Another wavelength may be selected depending on a measurement area of the observation target.

The light emitted from the light source 101-1 is guided to the optical coupler 131 through a single mode fiber 130-1 and split into the reference light 105 and the measuring light 106-1 in a ratio of 96:4. Polarization controllers 153-1 to 153-4 are provided on the respective single mode fibers.

(Reference Optical Path of AOSLO)

Next, an optical path of the reference light 105 is described.

The reference light 105 split by the optical coupler 131 enters a light intensity measuring apparatus 164 through an optical fiber 130-2. The light intensity measuring apparatus 164 is used for measuring light intensity of the reference light 105 so as to monitor the light intensity of the measuring light 106-1.

(Measuring Optical Path of AOSLO)

Next, an optical path of the measuring light 106-1 is described.

The measuring light 106-1 split by the optical coupler 131 is guided to a lens 135-4 through the single mode fiber 130-4, and is adjusted to be a collimated light beam having a beam diameter of 4 mm.

The measuring light 106-1 passes through a beam splitter 158-1 and lenses 135-5 to 135-6, and enters the spatial light modulator 159.

Here, the spatial light modulator 159 is controlled by a personal computer 125 via a spatial light modulator driver 188 in a driver unit 181.

Next, the measuring light 106-1 is modulated by the spatial light modulator 159, passes through lenses 135-7 and 135-8, and enters a mirror of the XY scanner 119-1. For simplification, the XY scanner 119-1 is illustrated as a single mirror. However, in an actual case, two mirrors, that is, an X scanner and a Y scanner, are disposed close to each other to raster-scan a retina 127 in a direction perpendicular to the optical axis. The center of the measuring light 106-1 is adjusted to align with each center of rotation of the mirrors of the XY scanner 119-1.

Here, the X scanner is a scanner for scanning the measuring light 106-1 in a direction parallel to the drawing sheet, and a resonance type scanner is used for the X scanner here. The drive frequency is approximately 7.9 kHz. In addition, the Y scanner is a scanner for scanning the measuring light 106-1 in a direction perpendicular to the drawing sheet, and a galvano scanner is used for the Y scanner here. The drive waveform is a sawtooth wave, the frequency is 64 Hz, and the duty ratio is 16%. The drive frequency of the Y scanner is an important parameter for determining a frame rate of the AOSLO image photography.

Here, the XY scanner 119-1 is controlled by the personal computer 125 through an optical scanner driver 182 included in the driver unit 181.

Lenses 135-9 and 135-10 correspond to an optical system for scanning the retina 127 and serve to scan the retina 127 with the measuring light 106-1 in a manner of pivoting on the vicinity of a cornea 126.

Here, the beam diameter of the measuring light 106-1 is 4 mm, but the beam diameter may be larger than 4 mm in order to acquire an optical image with higher resolution.

An electric stage 117 may be moved in a direction indicated by the arrows to adjust the position of the associated lens 135-10.

Here, the electric stage 117 is controlled by the personal computer 125 through an electric stage driver 183 included in the driver unit 181.

The position of the lens 135-10 may be adjusted, to thereby focus the measuring light 106-1 to a predetermined layer of the retina 127 of the eye to be inspected 107 to observe the layer. In other words, the structure including the lens 135-10 and the electric stage 117 as a focus adjustment unit according to the present invention allows the second measuring light and the measuring light 106-1 to focus on a desired layer of the retina of the eye to be inspected.

In addition, it is possible to support the case where the eye to be inspected 107 has ametropia.

The measuring light 106-1 enters the eye to be inspected 107 and is reflected or scattered by the retina 127 so as to be the return light 108, which is guided to the optical coupler 131 again, and reaches the detector 138-1 through a single mode fiber 130-3. As the detector 138-1, for example, an avalanche photo diode (APD) or a photomultiplier tube (PMT) is used, which is a high speed sensor with high sensitivity.

The return light 108 is modulated again by the spatial light modulator 159.

In addition, a part of the return light 108 split by the beam splitter 158-1 enters a wavefront sensor 155, and an aberration of the return light 108 generated in the eye to be inspected 107 is measured.

The wavefront sensor 155 is electrically connected to the personal computer 125.

Here, the lenses 135-5 to 135-10 and the like are disposed so that the cornea 126, the XY scanner 119-1, the wavefront sensor 155, and the spatial light modulator 159 are optically conjugate to each other.

Therefore, the wavefront sensor 155 can measure the aberration of the eye to be inspected 107. In addition, the spatial light modulator 159 can correct the aberration of the eye to be inspected 107.

Further, based on the obtained aberration as a measurement result of the wavefront sensor, the spatial light modulator 159 is controlled in real time so that the aberration generated in the eye to be inspected 107 is corrected, and hence a planar image with higher lateral resolution can be acquired.

In this embodiment, the lens 135-10 is a spherical lens, but a cylindrical lens may be used instead of the spherical lens 135-10 depending on an aberration (ametropia) of the eye to be inspected 107. An additional lens may be provided on the optical path of the measuring light 106-1.

Figure 1B:
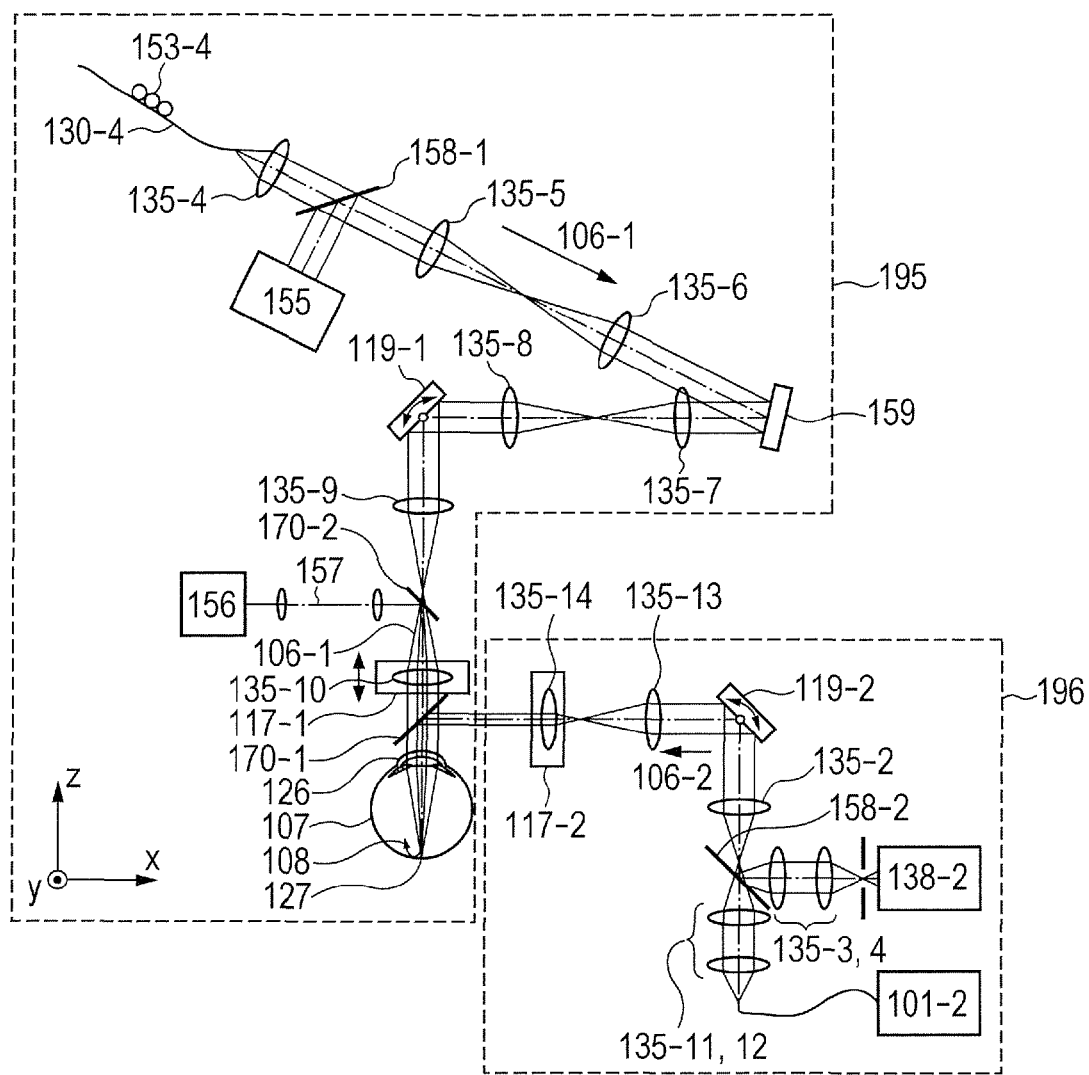
FIG. 1B is a diagram illustrating another structural example of the SLO apparatus.

Here, the lens 135-10 and the electric stage 117 are shared by the AOSLO unit 195 and the WFSLO unit 196. However, it is possible to dispose sets of the lens and the electric stage independently to the AOSLO unit 195 and the WFSLO unit 196 as illustrated in FIG. 1B. In this case, the electric stages of the AOSLO unit 195 and the WFSLO unit 196 may be operated in synchronization with each other.

In this embodiment, the measuring light 106-1 is used for measuring the aberration with the wavefront sensor 155. However, it is possible to use another light source for measuring the aberration. In addition, it is possible to form another optical path for measuring the aberration.

For instance, it is possible to use a beam splitter so that the light for measuring the aberration enters from between the spherical lens 135-10 and the cornea 126.

(Measurement System of AOSLO)

Next, a configuration of the measurement system is described.

The AOSLO apparatus 109 can acquire the planar image (SLO image) constituted of intensities of the return light 108 from the retina 127.

The return light 108 as light reflected or scattered by the retina 127 enters the detector 138-1 through the lenses 135-4 to 135-10, the spatial light modulator 159, the optical coupler 131, and the like, and the light intensity is converted into a voltage signal.

The voltage signal obtained by the detector 138-1 is converted into a digital value by an AD board 176 in the personal computer 125. The personal computer 125 performs data processing in synchronization with operation and the drive frequency of the XY scanner 119-1 so as to form the planar image. Here, the fetch speed of the AD board 176 is 15 MHz.

In addition, a part of the return light 108 split by the beam splitter 158-1 enters the wavefront sensor 155, and hence an aberration of the return light 108 is measured.

The wavefront sensor 155 is a Shack-Hartmann wavefront sensor having specifications of a measuring range as narrow as −1 D to +1 D and high measurement accuracy.

The obtained aberration is expressed by using a Zernike polynomial, which indicates the aberration of the eye to be inspected 107.

The Zernike polynomial includes a tilt (inclination) term, a defocus term, an astigmatism term, a coma term, and a trefoil term.

(Method of Acquiring AOSLO Image)

Next, a method of acquiring the planar image (AOSLO image) is described with reference to FIGS. 2A to 2D.

The AOSLO apparatus 109 controls the XY scanner 119-1 and acquires intensities of the return light 108 with the detector 138-1 so as to acquire the planar image of the retina 127. Now, a method of acquiring the planar image of the retina 127 (in the plane perpendicular to the optical axis) is described.

Figure 2A:
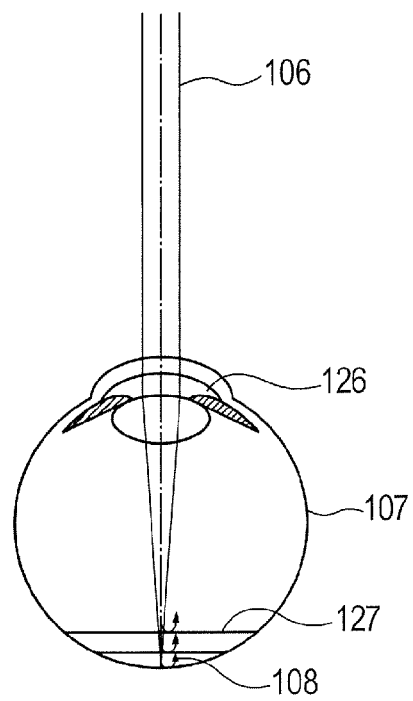
FIG. 2A is a diagram illustrating a method of acquiring an image by the SLO apparatus according to the first embodiment of the present invention, and is a diagram schematically illustrating a state where an eye to be inspected is observed by the SLO apparatus.

FIG. 2A is a schematic diagram of the eye to be inspected 107 and illustrates a state in which the eye to be inspected 107 is observed by the AOSLO apparatus 109.

As illustrated in FIG. 2A, the measuring light 106-1 enters the retina 127 through the cornea 126 and is reflected or scattered at various positions to be the return light 108, which reaches the detector 138-1.

Figure 2B:
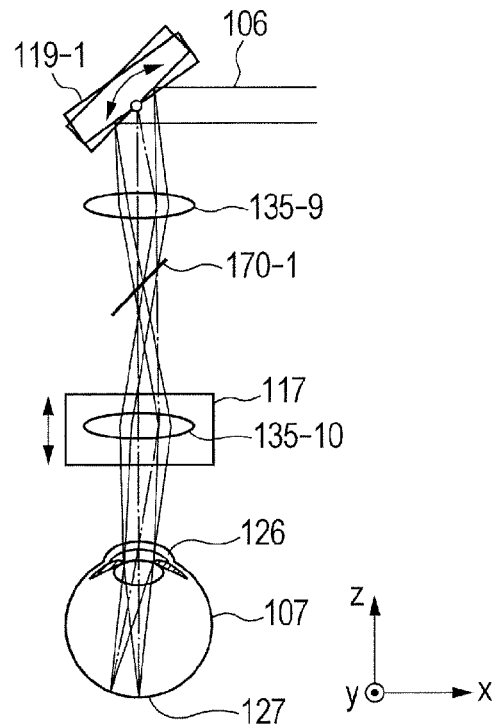
FIG. 2B is a diagram illustrating a manner in which a scanner scans the eye to be inspected with measuring light.

Further, as illustrated in FIG. 2B, the XY scanner 119-1 is driven in an X direction while detecting intensities of the return light 108, and hence information at individual positions in an X axis can be acquired.

Figure 2C:
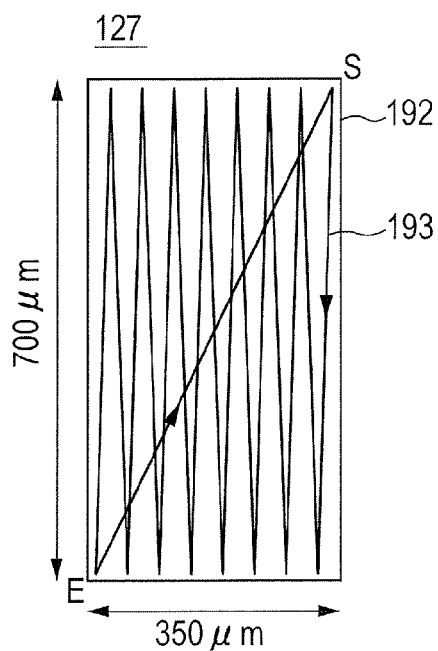
FIG. 2C is a diagram illustrating an example of a scan pattern in an imaging range.
Figure 2D:
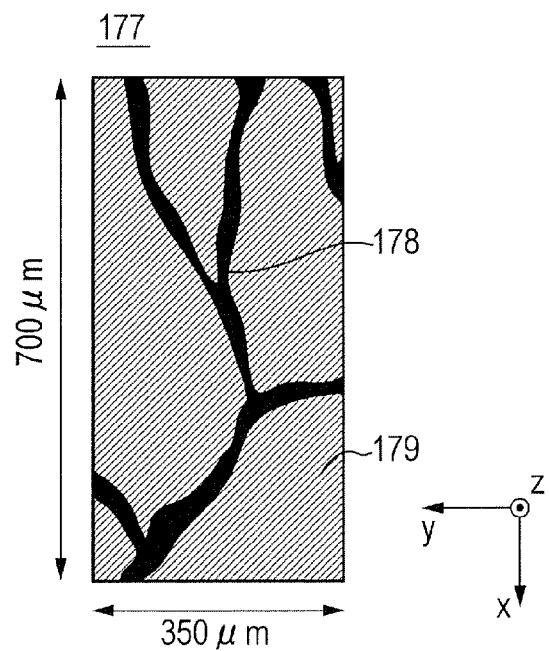
FIG. 2D is a diagram illustrating an example of an acquired image.

Further, as illustrated in FIG. 2C, the XY scanner 119-1 is driven simultaneously in the X axis direction and in the Y axis direction, and hence raster scan of the retina 127 in a photographing or imaging range 192 is performed with the measuring light 106-1 as indicated by a locus 193 so as to detect intensities of the return light 108. In this way, a two-dimensional distribution of intensities of the return light 108 is obtained, which is a planar image 177 (FIG. 2D).

Here, the measuring light 106-1 is scanned from an upper right point S to a lower left point E, and intensities of the return light 108 during the scanning are used for constituting the planar image 177. The locus 193 from the point E to the point S is preparation for the next photography of the planar image 177. The ratio of time period necessary for the scanning is 84% for the point S to the point E and 16% for the point E to the point S in the locus 193 illustrated in FIG. 2C, and this ratio is based on the duty ratio of the above-mentioned drive waveform of the Y scanner. In addition, for simple illustration, FIG. 2C illustrates the number of times of scanning in the X direction of the locus 193 to be smaller than in reality.

Here, the planar image 177 has a size of 700×350 μm, and a time period necessary for acquiring the planar image 177 is approximately 15.6 ms. The time period is based on the drive frequency of the Y scanner.

In addition, in the planar image 177, photoreceptor cells 179 having a relatively large intensity of the return light 108 are displayed brightly, while blood vessels 178 having a relatively small intensity are displayed darkly. In addition, blood corpuscles (not shown) in the blood vessel 178 are displayed brightly.

(Entire WFSLO Unit)

Next, an entire WFSLO unit is described.

The WFSLO unit basically has the same configuration as that of the AOSLO unit except that the WFSLO unit does not include the adaptive optics system and the reference optical path. Overlapping description of the same part is omitted.

Light emitted from a light source 101-2 is guided to the eye to be inspected 107 as the observation target through lenses 135, an XY scanner 119-2, a dichroic mirror 170-1, and the like.

(Light Source of WFSLO)

Next, details of the light source 101-2 are described. As with AOSLO, the light source 101-2 is an SLD. A wavelength of the light source 101-2 is 910 nm and a bandwidth thereof is 10 nm. Here, in order to separate the optical path of the AOSLO from the optical path of the WFSLO by using the dichroic mirror, the individual light sources have different wavelengths.

(Measuring Optical Path of WFSLO)

Next, an optical path of measuring light 106-2 is described.

The measuring light 106-2 emitted from the light source 101-2 is guided to the eye to be inspected 107 as the observation target through the lenses 135-1, 135-2, 135-11, and 135-12, the XY scanner 119-2, the dichroic mirror 170-1, and the like.

Here, an X scanner, which is the component of the XY scanner 119-2, is a scanner for scanning the measuring light 106-2 in a direction parallel to the drawing sheet, and a resonance type scanner is used for the X scanner here. The drive frequency is approximately 3.9 kHz. In addition, a Y scanner is a scanner for scanning the measuring light 106-2 in a direction perpendicular to the drawing sheet, and a galvano scanner is used for the Y scanner here. The drive waveform is a sawtooth wave, the frequency is 15 Hz, and the duty ratio is 16%. The drive frequency of the Y scanner is an important parameter for determining a frame rate of the WFSLO image photography or taking.

Here, the beam diameter of the measuring light 106-2 is 1 mm, but the beam diameter may be larger than 1 mm in order to acquire an optical image with higher resolution.

The measuring light 106-2 enters the eye to be inspected 107 and is reflected or scattered by the retina 127 so as to be return light 108-2, which reaches a detector 138-2 through the dichroic mirror 170-1, the lenses 135, the XY scanner 119-2, a beam splitter 158-2, and the like.

(Method of Acquiring WFSLO Image)

Next, a method of acquiring a wide field planar image (WFSLO image) is described.

The AOSLO apparatus 109 controls the XY scanner 119-2 and acquires intensities of the return light 108-2 with the detector 138-2 so as to acquire the wide field planar image of the retina 127. The method of acquiring the wide field planar image of the retina 127 (in the plane perpendicular to the optical axis) is the same as the method of acquiring the AOSLO image, and hence description thereof is omitted.

(AOSLO Image Acquiring Procedure)

Next, a method of acquiring the planar image by using the SLO apparatus as a feature of the present invention is described. The AOSLO apparatus 109 uses the WFSLO unit 196 so as to allow the measuring light 106-2 to focus on the retina 127 for photographing or imaging the WFSLO image. Further, the AOSLO apparatus 109 measures an optical aberration of the eye to be inspected 107 using the wavefront sensor 155 in a state where the measuring light 106-1 can be focused on the retina, and controls the spatial light modulator 159 so as to correct a wavefront aberration generated in the eye to be inspected 107. Thus, the planar image with higher lateral resolution can be acquired.

Here, because the optical aberration is measured by using the wavefront sensor 155 in the state where the above-mentioned measuring light 106-1 can be focused on the retina 127, there is little detected defocus component occupying most of the optical aberration of the eye to be inspected. Here, a unit for acquiring a planar image of the retina 127 of a shortsighted eye to be inspected 107 is described.

In the method of acquiring the planar image, the following steps (1) to (6) are performed successively, for example. Otherwise, it is possible to return to a former step as necessary. In addition, it is possible to use a computer or the like so as to automatically perform the following steps. FIG. 3 is a flowchart illustrating the method of acquiring the planar image. Note that, in the following flow, the WFSLO unit 196 corresponds to a first photographing or imaging unit, which irradiates the eye to be inspected 107 with the first measuring light 106-2, and uses return light thereof, namely the first return light 108-2 to acquire a first image. In addition, the AOSLO unit 195 corresponds to a second photographing or imaging unit, which irradiates the eye to be inspected 107 with the second measuring light 106-1, and uses return light thereof, namely the second return light 108-1 to acquire a second image.

Here, as the acquiring method, steps in the case of the structure illustrated in FIG. 1B are described.

(1) The WFSLO unit 196 is operated. The measuring light 106-2 enters the eye to be inspected 107 as a first step. Here, the position of a lens 135-14 is adjusted so that the measuring light 106-2 enters the eye to be inspected 107 in a state of a collimated beam. Here, a lighting position of the fixation lamp 156 is set so that a central fovea of the eye to be inspected 107 is displayed in the center of the WFSLO image.

(2) As a second step, the XY scanner 119-2 is driven so that the retina of the eye to be inspected 107 is scanned with the measuring light 106-2, and the return light 108-2 is used to acquire a signal of the detector 138-2 so that the WFSLO image is acquired.

(3) The step (2) is performed repeatedly, and the electric stage 117-2 is used to adjust the position of the lens 135-14 so that the WFSLO image becomes clearer. Then, the signal of the detector 138-2 is recorded. In other words, as a third step, the WFSLO image as the first image is referred to so as to adjust the layer on which the measuring light 106-2 is focused. Thus, an adjusted position of the focus adjustment unit (lens 135-14 in this embodiment) focused on a predetermined layer is obtained. Further, the obtained adjusted position is converted into a diopter scale of the eye to be inspected 107 based on an optical design value. This calculation of the diopter scale is performed by a module in the personal computer 125, which works as a diopter scale calculating unit for calculating a diopter scale of the eye to be inspected from the adjusted state of a first optical unit based on the optical design value of the first optical unit. Note that, this measuring light 106-2 corresponds to the first measuring light of the present invention, the above-mentioned focus adjustment unit for focusing the measuring light 106-2, which includes the lens 135-14 and the electric stage 117-2, corresponds to a first focus unit, and the WFSLO unit 196 for acquiring images corresponds to a first image acquiring unit.

(4) Setting of the fixation lamp 156 is performed. The lighting position corresponding to a desired position on the retina of the eye to be inspected 107 for which the AOSLO image is acquired is set for the fixation lamp 156. Next, the AOSLO unit 195 is operated. As a fourth step, the measuring light 106-1 enters the eye to be inspected 107. Next, the diopter scale of the eye to be inspected 107, which is obtained in the step (3), is converted into a position of the lens 135-10 based on the optical design value, and the position is adjusted by using the electric stage 117-1. This conversion is performed by a module in the personal computer 125, which works as an adjusted state calculating unit for calculating the adjusted state of the second optical unit based on the calculated diopter scale. Note that, the position of the lens 135-10 is calculated in consideration of rotation of the eye to be inspected 107 due to a change of the lighting position of the fixation lamp 156. By this adjustment, the measuring light 106-1 is focused on the retina 127. In other words, by referring to the adjusted state obtained in the third step, the state where the measuring light 106-1 is focused on the predetermined layer is obtained in advance. In this state, irradiation with the measuring light 106-1 is performed.

(5) A part of the return light 108 is measured by the wavefront sensor 155, which corresponds to an aberration measurement unit, so as to obtain an optical aberration of the eye to be inspected 107. The spatial light modulator 159, which corresponds to an aberration correction unit, is controlled to minimize the obtained wavefront aberration. In other words, as a fifth step, the aberration of the eye to be inspected is measured, and aberrations of the measuring light and the return light are corrected based on a result of the measurement. Here, feedback control is performed by using the wavefront sensor 155, the spatial light modulator 159, and the personal computer 125 to minimize the wavefront aberration. Thus, a surface shape of the spatial light modulator 159 is controlled in real time.

(6) The AOSLO image is acquired from the signal acquired by the detector 138-1 while driving the XY scanner 119-1.

Here, the example in which the step (5) and the step (6) are successively performed is described, but the steps may be performed simultaneously. Note that, in the above-mentioned structure, the spatial light modulator 159 corresponds to the aberration correction unit, and the measuring light 106-1 corresponds to the second measuring light. Further, the structure for focusing, which includes the lens 135-10 and the electric stage 117-1, corresponds to a second focus unit for focusing the second measuring light on the object to be inspected, and the AOSLO unit corresponds to a second image acquiring unit for acquiring a second image of an area corresponding to a part of the first image as a WFSLO image.

In addition, the personal computer 125 includes a module area working as the focus adjustment unit for adjusting a focus condition of the second focus unit based on a focus condition of the above-mentioned first focus unit.

As described above, the WFSLO unit successively acquires WFSLO images of a wide photographing or imaging range of the eye to be inspected, and a position of the lens is adjusted, which performs focusing of the measuring light of the AOSLO unit for a photographing or imaging range narrower than the photographing or imaging range of the WFSLO image, by using positional information of the lens for performing focus adjustment of the WFSLO measuring light. In this way, the aberration of the return light of the measuring light from the AOSLO unit scarcely contains substantially no defocus component. Therefore, a measurement range of an aberration amount required in the wavefront sensor is decreased. For instance, in order to measure an aberration of the eye to be inspected containing the defocus component, it is required to support diopter scales in the range of $-10$ D to $+5$ D, for example. However, it is sufficient to support diopter scales in the range of, for example, $-1$ D to $+1$ D in this embodiment. In the case of a Shack-Hartmann sensor as a typical wavefront sensor, the measurement range and the measurement accuracy have a trade-off relationship in principle. Therefore, by decreasing the measurement range, it is possible to improve the measurement accuracy.

In addition, by adjusting focus using an index of an image contrast or intensity of the WFSLO image, it is possible to easily perform the focus adjustment. In other words, it is preferred to determine the adjusted state of the first optical unit by using this index, which contains the contrast or intensity of the WFSLO image as the first image. In addition, it is possible to automatically adjust focus by using a computer. Note that, in this case, it is preferred that the personal computer 125 as a control apparatus of the present invention include a module area working as a focus condition acquiring unit for acquiring the contrast or the like of the WFSLO image as the focus condition of the first focus unit including the electric stage 117-2 and the focus lens 135-14. In addition, in this case, it is preferred that the focus adjustment unit adjust the focus condition of the second focus unit including the electric stage 117-1 and the lens 135-10 based on the contrast.

Further, in this case, the electric stage 117-2 may further include a structure as a moving unit for moving the lens 135-14 along the optical path based on the contrast of the WFSLO image, and the focus condition acquiring unit for acquiring the position of the lens 135-14 as the focus condition of the first focus unit. The focus adjustment unit may adjust the focus condition of the second focus unit based on the position of the lens 135-14.

In addition, it is possible to grasp the focus condition as a position of an optical member, namely a lens of the focus unit on the optical axis, or as an angle of the lens with respect to the optical axis. In this case, the position or the angle of the lens 135-14 in the first focus unit is calculated as a position or an angle of the lens 135-10 of the second focus unit and is reflected thereon.

Because the same lens is used for focus adjustment of the WFSLO unit and for focus adjustment of the AOSLO unit, it is possible to provide an apparatus having a simple structure.

By adjusting the lens for focus adjustment of the AOSLO unit and focusing the measuring light on a desired layer of the retina, it is possible to acquire an AOSLO image of the desired layer of the retina.

Note that, in the above-mentioned embodiment, there is exemplified a structure which includes the electric stage 117 and the lens 135-10 as the first optical unit for adjusting a focus position of the first measuring light 106-2. As the focus adjustment unit for obtaining the adjusted state of the electric stage 117 when the measuring light 106-2 is focused by controlling the above-mentioned structure, the driver unit 181 and the electric stage driver 183 are exemplified. Further, also as the second optical unit for adjusting the focus position of the second measuring light 106-1, the structure including the electric stage 117 and the lens 135-10 is exemplified. In other words, in the above-mentioned embodiment, the first focus unit as the first optical unit and the second focus unit as the second optical unit share a focus lens and a drive stage for supporting the focus lens and for driving the focus lens in the optical axis direction. However, the present invention is not limited to this embodiment. It is possible to dispose the first optical unit and the second optical unit individually. In this case, too, the focus adjustment unit only needs to control the second optical unit so that a satisfactory focus condition can be obtained by adjusting the focus position of the second optical unit appropriately depending on the adjusted state obtained by the first optical unit. In addition, as to the electric stage 117, there is exemplified an embodiment in which a position of the lens 135-10 on the optical axis is adjusted. However, it is possible to enable the lens 135-10 to rotate with respect to the optical axis so that the lens 135-10 corresponds to rotation of the eye to be inspected. In this case, the above-mentioned adjusted state includes not only the position but also the angle so that at least one of the position and the angle expresses the adjusted state.

Other Embodiment

Further, the present invention is also implemented by executing the following processing. Specifically, in this processing, software (program) for implementing the functions of the above-mentioned embodiment is supplied to a system or an apparatus via a network or various kinds of storage medium, and a computer (CPU, MPU, or the like) of the system or the apparatus reads out and executes the program.

In addition, the case where the object to be inspected is an eye is described in the above-mentioned embodiment. However, the present invention is not limited to the above-mentioned embodiment, but can be embodied with various changes and modifications without departing from the spirit of the present invention. For instance, although the object to be measured is an eye in the above-mentioned embodiment, the present invention can be applied to an object to be measured other than an eye, such as skin or an organ.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-035088, filed Feb. 21, 2012, and Japanese Patent Application No. 2012-273761, filed Dec. 14, 2012, which are hereby incorporated by reference herein in their entirety.

What is claimed is:

1. An imaging apparatus, comprising:
   a first image acquiring unit for acquiring a first image of an object to be inspected based on first return light from the object to be inspected irradiated with first measuring light via a first focus member for focusing the first measuring light on the object to be inspected;
   a first electric stage configured to move the first focus member;
   a second image acquiring unit, including an aberration correction unit, for acquiring a second image of an area corresponding to a part of the first image of the object to be inspected based on second return light from the object to be inspected irradiated with second measuring light via a second focus member for focusing the second measuring light on the object to be inspected;
   a second electric stage configured to move the second focus member;
   a changing unit configured to change a lighting position of a fixation lamp; and
   a focus adjustment unit for (a) adjusting a focus condition of the first focus member and a focus condition of the second focus member by controlling the first electric stage and the second electric stage to respectively move the first focus member and the second focus member in synchronization with each other, (b) controlling the aberration correction unit after the first focus member and the second focus member are moved in synchronization with each other, and (c) adjusting, after changing the lighting position of the fixation lamp, the focus condition of the second focus member by controlling the second electric stage to move the second focus member independently.

2. An imaging apparatus according to claim 1, further comprising a focus condition acquiring unit for acquiring a contrast of the first image,
   wherein the focus adjustment unit adjusts the focus condition of the first focus member and the focus condition of the second focus member by controlling, based on the contrast of the first image, the first electric stage and the second electric stage to respectively move the first focus member and the second focus member in synchronization with each other.

3. An imaging apparatus according to claim 1, wherein the focus adjustment unit adjusts the focus condition of the first focus member and the focus condition of the second focus member by controlling, based on the first return light, the first electric stage and the second electric stage to respectively move the first focus member and the second focus member in synchronization with each other.

4. An imaging apparatus according to claim 1, wherein an adjusted state of at least one of the first focus member and the second focus member is expressed by one of a position of one of the first focus member and the second focus member on an optical axis and an angle of one of the first focus member and the second focus member with respect to the optical axis.

5. An imaging apparatus according to claim 4, wherein the one of the position and the angle of the second focus member is calculated based on the one of the position and the angle of the first focus member in an adjusted state where the first measuring light is focused on the object to be inspected.

6. An imaging apparatus according to claim 1, wherein a first imaging range of the first image acquiring unit for the object to be inspected is set wider than a second imaging range of the second image acquiring unit for the object to be inspected.

7. An imaging apparatus according to claim 1, wherein the object to be inspected comprises an eye to be inspected.

8. An imaging apparatus according to claim 7, wherein one of a position of the second focus member on an optical axis and an angle of the second focus member with respect to the optical axis is calculated in consideration of a lighting position of a fixation lamp for prompting the eye to be inspected to rotate.

9. An imaging apparatus according to claim 1, further comprising:
an adjusted state calculating unit for calculating an adjusted state of the second focus member based on optical design values of the first focus member and the second focus member,
wherein the focus adjustment unit adjusts the focus condition of the second focus member by controlling, based on the calculated adjusted state and the first return light, the second electric stage to move the second focus member.

10. An imaging apparatus according to claim 1, wherein the object to be inspected comprises an eye to be inspected, and
wherein the focus adjustment unit adjusts, after changing the lighting position of the fixation lamp, the focus condition of the second focus member by controlling the second electric stage to focus the second measuring light on a desired layer of a retina of the eye to be inspected.

11. An imaging apparatus according to claim 1, wherein adjustment of one of a position of at least one of the first focus member and the second focus member on an optical axis and an angle of the at least one of the first focus member and the second focus member with respect to the optical axis is performed by using an electric stage.

12. An imaging apparatus according to claim 1, wherein the second image acquiring unit includes an aberration measuring unit configured to measure an aberration of the second return light from the object to be inspected, and
wherein the focus adjustment unit controls the aberration correction unit in real time based on the measured aberration, after the first focus member and the second focus member are moved in synchronization with each other.

13. An imaging apparatus according to claim 1 wherein the first image acquiring unit includes a first scanning unit configured to scan the first measuring light on the object to be inspected, and continuously acquires a WF-SLO image as the first image by using the first scanning unit when the first focus member and the second focus member are moved in synchronization with each other, and
wherein the second image acquiring unit includes a second scanning unit configured to scan the second measuring light on an area on the object to be inspected smaller than an area on which the first measuring light is scanned, and acquires an AO-SLO image as the second image by using the second scanning unit and the aberration correction unit after the first focus member and the second focus member are moved in synchronization with each other.

14. An imaging method, comprising:
acquiring a first image of an object to be inspected based on first return light from the object to be inspected irradiated with first measuring light via a first focus member for focusing the first measuring light on the object to be inspected;
acquiring, by using an aberration correction unit, a second image of an area corresponding to a part of the first image of the object to be inspected based on second return light from the object to be inspected irradiated with second measuring light via a second focus member for focusing the second measuring light on the object to be inspected;
changing a lighting position of a fixation lamp;
adjusting a focus condition of the first focus member and a focus condition of the second focus member by controlling a first electric stage and a second electric stage to respectively move the first focus member and the second focus member in synchronization with each other;
controlling the aberration correction unit after the first focus member and the second focus member are moved in synchronization with each other; and
adjusting, after changing the lighting position of the fixation lamp, the focus condition of the second focus member by controlling the second electric stage to move the second focus member independently.

15. A non-transitory computer program for causing a computer to perform the steps of the imaging method according to claim 14.

16. An imaging method according to claim 14, wherein the focus condition of the first focus member and the focus condition of the second focus member are adjusted by controlling, based on the first return light, the first electric stage and the second electric stage to respectively move the first focus member and the second focus member in synchronization with each other.

17. An imaging method according to claim 14, further comprising measuring an aberration of the second return light from the object to be inspected,
wherein the aberration correction unit is controlled in real time based on the measured aberration, after the first focus member and the second focus member are moved in synchronization with each other.

18. An imaging method according to claim 14, wherein a WF-SLO image is continuously acquired as the first image by using a first scanning unit which scans the first measuring light on the object to be inspected, when the first focus member and the second focus member are moved in synchronization with each other, and
wherein an AO-SLO image is acquired as the second image by using (a) a second scanning unit which scans the second measuring light on an area on the object to be inspected smaller than an area on which the first measuring light is scanned, and (b) the aberration correction unit, after the first focus member and the second focus member are moved in synchronization with each other.

19. An imaging apparatus comprising:
a first image acquiring unit for acquiring a first image of an object to be inspected based on first return light from the object to be inspected irradiated with first measuring light via a first focus member for focusing the first measuring light on the object to be inspected;
a second image acquiring unit including an aberration correction unit, for acquiring a second image of an area corresponding to a part of the first image of the object to be inspected based on second return light from the object to be inspected irradiated with second measuring light via a second focus member for focusing the second measuring light on the object to be inspected;
a changing unit configure to change a lighting position of a fixation lamp; and
a control unit for (a) controlling a focus condition of the first focus member and a focus condition of the second focus member in synchronization with each other, (b) controlling the aberration correction unit after the focus condition of the first focus member and the focus condition of the second focus member are controlled in synchronization with each other, and (c) controlling, after changing the lighting position of the fixation lamp, the focus condition of the second focus member independently.

20. An imaging apparatus according to claim 19, wherein the control unit controls, based on the first return light, the focus condition of the first focus member and the focus condition of the second focus member in synchronization with each other.

21. An imaging apparatus according to claim 19, wherein the second image acquiring unit includes an aberration measuring unit configured to measure an aberration of the second return light from the object to be inspected, and
wherein the control unit performs a feedback control by controlling the aberration correction unit in real time based on the measured aberration after the focus condition of the first focus member and the focus condition of the second focus member are controlled in synchronization with each other.

22. An imaging apparatus according to claim 19, wherein the first image acquiring unit includes a first scanning unit configured to scan the first measuring light on the object to be inspected, and continuously acquires a WF-SLO image as the first image by using the first scanning unit when the focus condition of the first focus member and the focus condition of the second focus member are controlled in synchronization with each other, and
wherein the second image acquiring unit includes a second scanning unit configured to scan the second measuring light on an area on the object to be inspected smaller than an area on which the first measuring light is scanned, and acquires an AO-SLO image as the second image by using the second scanning unit and the aberration correction unit after the focus condition of the first focus member and the focus condition of the second focus member are controlled in synchronization with each other.

23. An imaging method comprising:
acquiring a first image of an object to be inspected based on first return light from the object to be inspected irradiated with first measuring light via a first focus member for focusing the first measuring light on the object to be inspected;
acquiring, by using an aberration correction unit, a second image of an area corresponding to a part of the first image of the object to be inspected based on second return light from the object to be inspected irradiated with second measuring light via a second focus member for focusing the second measuring light on the object to be inspected;
changing a lighting position of a fixation lamp;
controlling a focus condition of the first focus member and a focus condition of the second focus member in synchronization with each other;
controlling the aberration correction unit after the focus condition of the first focus member and the focus condition of the second focus member are controlled in synchronization with each other; and
controlling, after changing the lighting position of the fixation lamp, the focus condition of the second focus member independently.

24. A non-transitory computer program for causing a computer to perform the steps of the imaging method according to claim 23.

25. An imaging method according to claim 23, wherein the focus condition of the first focus member and the focus condition of the second focus member are controlled in synchronization with each other based on the first return light.

26. An imaging method according to claim 23, further comprising measuring an aberration of the second return light from the object to be inspected,
wherein a feedback control is performed by controlling the aberration correction unit in real time based on the measured aberration after the focus condition of the first focus member and the focus condition of the second focus member are controlled in synchronization with each other.

27. An imaging method according to claim 23, wherein a WF-SLO image is continuously acquired as the first image by using a first scanning unit which scans the first measuring light on the object to be inspected, when the focus condition of the first focus member and the focus condition of the second focus member are controlled in synchronization with each other, and
wherein an AO-SLO image is acquired as the second image by using (a) a second scanning unit which scans the second measuring light on an area on the object to be inspected smaller than an area on which the first measuring light is scanned, and (b) the aberration correction unit, after the focus condition of the first focus member and the focus condition of the second focus member are controlled in synchronization with each other.

* * * * *